United States Patent
Antoni-Zimmermann et al.

(10) Patent No.: US 6,846,777 B2
(45) Date of Patent: Jan. 25, 2005

(54) SYNERGISTIC BIOCIDAL COMPOSITION

(75) Inventors: Dagmar Antoni-Zimmermann, Speyer (DE); Rüdiger Baum, Waghäusel (DE); Thomas Wunder, Neustadt/Weinstrasse (DE); Hans-Jürgen Schmidt, Speyer (DE)

(73) Assignee: Thor GmbH, Speyer (DE)

( * ) Notice: Subject to any disclaimer, the term of this patent is extended or adjusted under 35 U.S.C. 154(b) by 0 days.

(21) Appl. No.: 10/344,224

(22) PCT Filed: Aug. 20, 2001

(86) PCT No.: PCT/EP01/09581

§ 371 (c)(1),
(2), (4) Date: Feb. 10, 2003

(87) PCT Pub. No.: WO02/15693

PCT Pub. Date: Feb. 28, 2002

(65) Prior Publication Data

US 2003/0199490 A1 Oct. 23, 2003

(30) Foreign Application Priority Data

Aug. 21, 2000  (DE) .......................... 100 40 814

(51) Int. Cl.⁷ .......................... A01N 43/40; A01N 43/80
(52) U.S. Cl. .................. 504/126; 504/130; 504/138; 504/155; 504/156; 514/188; 514/345; 514/372
(58) Field of Search ................. 504/126, 130, 504/138, 152, 155, 156; 514/188, 345, 372

(56) References Cited

U.S. PATENT DOCUMENTS

| | | | |
|---|---|---|---|
| 5,227,156 A | 7/1993 | Wiese | 424/70 |
| 5,464,622 A | 11/1995 | Mehta et al. | |
| 5,939,203 A | * 8/1999 | Kappock et al. | 428/469 |
| 6,228,382 B1 | * 5/2001 | Lindner et al. | 424/405 |

FOREIGN PATENT DOCUMENTS

| | | | |
|---|---|---|---|
| EP | 0 492 811 | | 11/1991 |
| JP | 04353836 | | 12/1992 |
| JP | 05099195 | | 4/1993 |
| JP | 11-228302 | * | 8/1999 |
| WO | WO 98/21962 | | 5/1998 |
| WO | WO/00/59305 | | 10/2000 |
| WO | WO /01/ 41570 | | 6/2001 |

* cited by examiner

Primary Examiner—S. Mark Clardy
(74) Attorney, Agent, or Firm—Hedman & Costigan, P.C.

(57) ABSTRACT

The invention relates to a biocidal composition which can be added to materials which can be attacked by harmful microorganisms, containing pyrithione as a biocidal active ingredient. The biocidal composition is characterised in that it contains 2-alkyl isothiazoline-3-one as another biocidally active ingredient. The active ingredients of the biocidal composition behave synergistically and are ideally suitable for controlling bacteria, fungus and algae.

11 Claims, No Drawings

SYNERGISTIC BIOCIDAL COMPOSITION

This application is a 371 of PCT/EP01/09581 filed Aug. 20, 2001.

The invention relates to a biocide composition, comprising a pyrithione as biocidal active ingredient, as additive to materials capable of being attacked by harmful microorganisms. In particular, the invention relates to a biocide composition which, being an algicidal and fungicidal composition, is suitable for preserving industrial objects and materials.

Biocidal compositions are employed in many fields, for example in the control of harmful algae, fungi and bacteria. The large number of biocidal active ingredients include, for example, zinc pyrithione and sodium pyrithione, as can be seen from U.S. Pat. No. 5,562,995 and JS 5883154. The first publication relates, inter alia, to avoiding an undesired discoloration in an aqueous antimicrobial mixture comprising both iron or copper ions and pyrithione as antimicrobial active ingredient. Discoloration is avoided by the addition of zinc ions. The second publication relates, inter alia, to preventing or eliminating undesired discoloration of an antimicrobial mixture comprising a resin, iron or copper ions and pyrithione by the addition of zinc ions.

Also, biocide compositions comprising as biocidal active ingredient, an iodopropargyl carbamate have already been described in WO 96/39836.

The biocidal action of 2-n-octylisothiazolin-3-one, which, in accordance with EP-0676140-A1 is employed for example as a mixture with methylisothiazolin-3-one, has furthermore also been reported.

Another fungicide which is commercially available is 4,5-dichloro-2-n-octyl-4-isothiazolin-3-one, for example under the name "Rozone® 2000" from Rohm & Haas Company or under the name "ACTICIDE®" DT from Thor GmbH.

The Japanese patent application 1992/353836 describes a microbicidal composition which comprises zinc 2-pyridionthiol 1-oxide, that is to say zinc pyrithione, and, for example, 3-iodo-2-propynyl butylcarbamate.

Furthermore, the Japanese patent application 1993/99195 describes a textile material which is finished with a composition for controlling fungal growth on the textile fibers. This composition comprises the 3-iodo-2-propynyl ester of N-n-butylcarbamic acid, that is to say 3-iodo-2-propynyl N-butylcarbamate, and, for example, bis(2-pyridylthio-1-oxidono)zinc, that is to say zinc pyrithione.

Also, U.S. Pat. No. 5,464,622 states antimicrobial compositions comprising the zinc salt of 2-mercaptopyridine N-oxide, that is to say zinc pyrithione, and iodopropargyl butylcarbamate.

Finally, WO 98/21962 relates to algicidal compositions comprising a mixture of zinc pyrithione and a halopropynyl compound, for example 3-iodo-2-propynyl butylcarbamate.

Nothing is mentioned in the prior art about compositions which, in addition to zinc pyrithione, also comprise an octyl isothiazolin-3-one.

The known biocide compositions comprising one of the above-mentioned biocidal active ingredients are not yet satisfactory for certain applications. This applies in particular to their use as preservatives for imparting biocidal properties to objects or coatings whose surfaces are frequently attacked by algae or fungi, as experience has shown. Attack by algae or fungi not only makes surfaces visually unattractive, but may also lead to damage to the material and to a reduced usable life of the objects and surfaces in question. Microbial attack of objects or coatings applied thereto is found in particular in locations where moisture levels are high, both in interior situations, for example in buildings of the food industry, of dairies or breweries, and in exterior situations, especially on buildings which are exposed to unfavorable climatic conditions, for example on facades with lacking insolation. In particular, coatings comprising one of the above-mentioned biocidal active ingredients, exhibit inadequate resistance to colonization by, for example, Alternaria species or other fungi from the group of what are known as "sooty molds". Firstly, microbial growth leads to visual impairment and discoloration which is associated therewith. Secondly, various biocidal active ingredients tend to discoloration when exposed to the effect of UV radiation.

Finally, it is desired to achieve, on the one hand, as potent a biocidal action as possible with the active ingredients and, on the other hand, to have to employ only relatively small amounts of the active ingredients for this purpose.

The invention is therefore based on the object of indicating a biocide composition which is improved by the fact that its components interact synergistically in the above-mentioned industrial materials and objects, in particular in coating systems, such as paints, varnishes and renders and can therefore be used in lower concentrations than in the case of the individual components for providing protection against attack and destruction by microorganisms. Preferably, the biocide composition should be active against bacteria, fungi and algae, in particular against molds, yeasts, wood-destroying and wood-discoloring fungi, and against algae, furthermore in the antifouling sector against relevant marine organisms, such as Balus, Ascidia, Serpula, Mytilus, Spirorbis, Bugula and Hydrazoa. In this context, the biocide composition should show activity against Alternaria species and other fungi from the group of what are known as the "sooty molds" and also show the highest possible degree of stability to discoloration owing to the effect of UV light and high temperatures.

This object is achieved by the invention by a biocide composition comprising a pyrithione (2-pyridinethiol 1-oxide) as biocidal active ingredient. The composition is characterized in that it comprises a 2-alkylisothiazolin-3-one as further biocidal active ingredient.

The biocide composition according to the invention is particularly suitable as algicidal and fungicidal composition for preserving industrial materials which are susceptible to microbial attack. Examples of such materials which are intended to be protected, by this biocide composition, from microbial change or destruction, are coating systems such as colors, varnishes, renders or antifouling paints, and plastic materials, cooling lubricants, heat-transfer fluids, glues, sizers, paper and board, leather, textiles and wood.

Examples of microorganisms which colonize industrial materials and objects of the above-mentioned type are representatives of the following genera:

*Alternaria*, such as *Alternaria alternata,*
*Aspergillus*, such as *Aspergillus niger,*
*Aureobasidium*, such as *Aureobasidium pullulans,*
*Chaetomium*, such as *Chaetomium globosum,*
*Coniophora*, such as *Coniophora puteana,*
*Cladosporium*, such as *Cladosporium cladosporoides,*
*Candida*, such as *Candida albicans,*
*Lentinus*, such as *Lentinus tigrinus,*
*Penicillium*, such as *Penicillium funiculosum,*
*Rhodotorula*, such as *Rhodotorula rubra,*
*Sclerophoma*, such as *Sclerophoma pityophila,*
*Trichoderma*, such as *Trichoderma viride,*

*Ulocladium*, such as *Ulocladium atrum*,
*Escherichia*, such as *Escherichia coli*,
*Pseudomonas*, such as *Pseudomonas aeruginosa*,
*Staphylococcus*, such as *Staphylococcus aureus*.

The biocide composition according to the invention, which is particularly suitable as preservative for coating systems, has the following positive characteristics:

a) good algicidal action;
b) good fungicidal action;
c) good activity against *Alternaria* species and other problem microorganisms which are difficult to inactivate in the field of preservation, in particular film preservation and the protection of materials, for example in coatings in the form of paints, including antifouling paints, varnishes and renders, and for the protection of timber, leather and plastics;
d) good persistence, even when subjected to potent leaching conditions and exposure to UV light, high temperatures, extreme weather conditions and climatic conditions, and conditions of changing weather;
e) biocidal long-term action despite low concentration of the biocide composition employed;
f) low toxicity to humans and mammals;
g) very low vapor pressure of the biocidal active ingredients;
h) favorable price/performance ratio.

The biocide composition according to the invention is distinguished by the fact that the mixture of a pyrithione and a 2-alkylisothiazolin-3-one results in a synergistic biocidal action. This allows for example that, in the case of good algicidal action being desired, an additional algicide can be dispensed with.

In accordance with the invention, the pyrithione is preferably present in the biocide composition in the form of zinc pyrithione or sodium pyrithione. However, copper pyrithione and iron pyrithione may also be employed. The last-mentioned two compounds show pronounced intrinsic color and are therefore only suitable for specific applications, for example antifouling.

Also, it is advantageous when the pyrithione is present in a concentration of from 0.1 to 99.9% by weight and the 2-alkylisothiazolin-3-one, also in the form of a mixture of two or more 2-alkylisothiazolin-3-ones, in a concentration of from 0.1 to 99.9% by weight, in each case based on the entire biocide composition.

In the 2-alkylisothiazolin-3-one the alkyl radical denotes an n-alkyl, i-alkyl or c-alkyl radical. Preferably, the alkyl radical comprises 1 to 10, in particular 1 to 8, carbon atoms. Especially preferred are 2-n-octylisothiazolin-3-one and 4,5-dichloro-2-n-octylisothiazolin-3-one.

The biocide composition according to the invention preferably comprises the pyrithione and the 2-alkylisothiazolin-3-one in a weight ratio of from 1:1 000 to 1 000:1, in particular of from 1:99 to 99:1, especially preferably of from 1:10 to 10:1, very especially preferably of from 1:3 to 3:1.

It has emerged that the synergism in the biocidal action of the composition according to the invention with a pyrithione and a 2-alkylisothiazolin-3-one as active ingredients can be increased further when the composition additionally comprises an iodoalkyl carbamate, in particular 3-iodo-2-propynyl N-butylcarbamate, as supplementary biocidal active ingredient.

In a particular embodiment, the biocide composition according to the invention deliberately contains no iodoalkyl carbamate in addition to the pyrithione and the 2-alkylisothiazolin-3-one.

It is expedient to employ, in the systems which are susceptible to microbial attack, the biocidal active ingredients of the composition according to the invention in combination with a polar or unpolar liquid medium. In this context, this medium may, for example, already exist in the biocide composition and/or in the system to be preserved.

Preferred polar liquid media are alcohols, esters, glycols, glycol ethers, glycol esters and 2,2,4-trimethyl-1,3-pentanediol monoisobutyrate (available under the trade name "Texanol" from Eastman Chemical Company).

Preferred unpolar liquid media are aromatics, such as alkylbenzenes, for example xylene and toluene, paraffins, unpolar esters, such as phthalates and fatty acid esters, epoxidized fatty acids and their derivatives, and silicone oils.

The biocide composition according to the invention preferably has a pH value in the range of from 4 to 10, in particular in the range of from 6 to 8.

The above-mentioned biocidal active ingredients, viz. the pyrithione, which is present, for example, in the form of zinc, sodium, copper and/or iron pyrithione, and the iodoalkyl carbamate, for example, in the form of 3-iodo-2-propynyl N-butylcarbamate, 3-iodo-2-propynyl N-hexylcarbamate, 3-iodo-2-propynyl N-cyclohexylcarbamate and/or 3-iodo-2-propynyl N-phenylcarbamate, and the 2-n-octylisothiazolin-3-one and/or the 4,5-dichloro-2-n-octylisothiazolin-3-one, are known substances and can be prepared by prior-art processes.

In addition, the biocide composition according to the invention may comprise one or more other biocidal active ingredients which are selected as a function of the specific system to be preserved. Examples of such other biocidal active ingredients are stated hereinbelow:

triazoles such as amitrol, azocyclotin, BASF 480P, bitertanol, difenoconazol, fenbuconazol, fenchlorazol, fenethanil, fluquinconazol, flusilazol, flutriafol, imibenconazole, isozofos, myclobutanil, metconazole, epoxyconazole, paclobutrazole, penconazole, propioconazole, (±)-cis-1-(4-chlorophenyl)-2-(1H-1,2,4-triazol-1-yl)cycloheptanol, tetraconazole, triadimefon, triadimenol, triapenthenol, triflumizol, triconazole and uniconazole, and the metal salts and acid adducts of these triazoles;

imidazoles, such as imazalil, pefurazoat, prochloraz, triflumizol and 2-(1-t-butyl)-1-(2-chlorophenyl)-3-(1,2,4-triazol-1-yl)propan-2-ol, and the metal salts and acid adducts of these imidazoles;

thiazolecarboxanilides, such as 2',6'-dibromo-2-methyl-4-trifluoromethoxy-4'-trifluoromethyl-1,3-thiazole-5carboxanilide, and the metal salts and acid adducts of these thiazolecarboxanilides;

methyl (E)-2-{2-[6-(2-cyanophenoxy)pyrimidin-4-yloxy]-phenyl}-3-methoxyacrylate, methyl (E)-2-{2-[6-(2-thioamidophenoxy) pyrimidin-4-yloxy]phenyl}-3-methoxyacrylate, methyl (E)-2-{2-[6-(2-fluorophenoxy)pyrimidin-4-yloxy]phenyl}-3-methoxyacrylate, methyl (E)-2-{2-[6-(2,6-difluorophenoxy) pyrimidin-4-yloxy]phenyl}-3-methoxyacrylate, methyl (E)-2-{2-[3-(pyrimidin-2-yloxy)phenoxy]phenyl}-3-methoxyacrylate, methyl (E)-2-{2-[3-(5-methylpyrimidin-2-yloxy)-phenoxy]phenyl}-3-methoxyacrylate, methyl (E)-2-{2-[3-(phenylsulfonyloxy)phenoxy]phenyl}-3-methoxyacrylate, methyl (E)-2-{2-[3-(4-nitrophenoxy)phenoxy]phenyl}-3-methoxyacrylate, methyl (E)-2-(2-phenoxy)-3-methoxyacrylate, methyl (E)-2-[2-(3,5- dimethylbenzoyl)pyrrol-1-yl]-3-methoxyacrylate, methyl (E)-2-[2-(3-methoxyphenoxy)phenyl]-3,-methoxyacrylate, methyl (E)-2-[2-(2-phenylethen-1-yl)phenyl]-3-methoxyacrylate, methyl (E)-2-[2-(3,5-dichlorophenoxy)pyridin-3-yl]-3-methoxyacrylate, methyl (E)-2-{2-[3-(1,1,2,2-tetrafluoroethoxy)phenoxy]phenyl}-3-methoxyacrylate, methyl (E)-2-{2-[3-α-hydroxybenzyl) phenoxy]phenyl}-3-methoxyacrylate, methyl (E)-2-[2-(4-phenoxypyridin-2-yloxy)phenyl]-3-methoxyacrylate, methyl (E)-2-[2-(3-n-propyloxyphenoxy)phenyl]-3-methoxyacrylate, methyl (E)-2-[2-(3-isopropyloxyphenoxy)phenyl]-3-methoxyacrylate, methyl (E)-2-{2-[3-(2-fluorophenoxy)phenoxy]phenyl}-3-methoxyacrylate, methyl (E)-2-[2-(3-ethoxyphenoxy)phenyl]-3-methoxyacrylate, methyl (E)-2-[2-(4-t-butylpyridin-2-yloxy)phenyl]-3-methoxyacrylate, methyl (E)-2-{2-[3-(3-cyanophenoxy) phenoxy]phenyl}-3-methoxyacrylate, methyl (E)-2-[2-(3-methylpyridin-2-yloxymethyl)phenyl]-3-methoxyacrylate, methyl (E)-2-{2-[6-(2-methylphenoxy)pyrimidin-4-yloxy]phenyl}-3-methoxyacrylate, methyl (E)-2-[2-(5-bromopyridin-2-yloxymethyl)phenyl]-3-methoxyacrylate, methyl (E)-2-{2-[3-(3-iodopyridin-2-yloxy)phenoxy]phenyl}-3-methoxyacrylate, methyl (E)-2-{2-[6-(2-chloropyridin-3-yloxy)pyrimidin-4-yloxy]phenyl}-3-methoxyacrylate, methyl (E,E)-2-[2-[5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxyacrylate, methyl (E,E)-2-{2-[(3-methoxyphenyl) methyloximinomethyl]phenyl}-3-methoxyacrylate, methyl (E)-2-{2-[6-(2-azidophenoxy)pyrimidin-4-yloxy]phenyl}-3-methoxyacrylate, methyl (E,E)-2-{2-[6-(phenylpyrimidin-4-yl)methyloximinomethyl]phenyl}-3-methoxyacrylate, methyl (E,E)-2-{2-[(4-chlorophenyl)methyloximinomethyl]phenyl}-3-methoxyacrylate, methyl (E)-2-{2-[6-(2-n-propylphenoxy)-1,3,5-triazin-4-yloxy]phenyl}-3-methoxyacrylate, methyl (E,E)-2-{2-[(3-nitrophenyl)methyloximinomethyl]phenyl}-3-methoxyacrylate;

succinate dehydrogenase inhibitors such as fenfuram, furcarbanil, cyclafluramid, furmecyclox, Seedvax, Metsulfovax, pyrocarbolid, oxycarboxin, Shirlan, mebenil (mepronil), benodanil and flutolanil (Moncut);

naphthalene derivatives such as terbinafin, naftifin, butenafin, 3-chloro-7-(2-aza-2,7,7-trimethyloct-3-en-5-ine);

sulfenamides, such as dichlorofluanid, tolylfluanid, folpet and fluorfolpet;

captan, captofol;

benzimidazoles, such as carbendazim, benomyl, furathiocarb, fuberidazole, thiophanate-methyl and thiabendazole and their salts;

morpholin derivatives such as tridemorph, fenpropimorph, falimorph, dimethomorph, dodemorph, allimorph and fenpropidin, and their salts with arylsulfonic acids, for example with p-toluenesulfonic acid and p-dodecylphenylsulfonic acid;

dithiocarbamates, cufraneb, ferbam, mancopper, mancozeb, maneb, metam, metiram, thiramzeneb, ziram;

benzothiazoles, such as 2-mercaptobenzothiazole;

benzamides, such as 2,6-dichloro-N-(4-trifluoromethylbenzyl)benzamide;

boron compounds, such as boric acid, borates and borax;

formaldehyde and formaldehyde donor compounds, such as benzyl alcohol mono(poly)hemiformal, oxazolidins, hexahydro-S-triazines, N-methylolchloroacetamide, paraformaldehyde, nitropyrine, oxolinic acid, tecloftalam;

biguanides, such as polyhexamethylene biguamide;

tris-N-(cyclohexyldiazeniumdioxy)aluminum, N-(cyclohexyldiazeniumdioxy)tributyltin and potassium salts thereof, bis-N-(cyclohexyldiazeniumdioxy) copper;

N-methylisothiazolin-3-one, 5-chloro-N-methylisothiazolin-3-one, 4,5-trimethyleneisothiazolinone, 1,2-benzoisothiazolinone, N-methylolchloroacetamide;

aldehydes, such as cinnamaldehyde, glutaraldehyde and β-bromocinnamaldehyde;

thiocyanates, such as thiocyanatomethylthiobenzothiazole and methylenebisthiocyanate;

quaternary ammonium compounds, such as benzyldimethyltetradecylammonium chloride, benzyldimethyldodecylammonium chloride and didecyldimethylammonium chloride;

iodine derivatives, such as diiodomethyl p-tolyl sulfone, 3-iodo-2-propynyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol;

phenol derivatives, such as tribromophenol, tetrachlorophenol, 3-methyl-4-chlorophenol, 3,5-dimethyl-4-chlorophenol, phenoxyethanol, dichlorophen, o-phenylphenol, m-phenylphenol, p-phenylphenol and 2-benzyl-4-chlorophenol, and the alkali and alkaline earth metal salts of these phenol derivatives;

microbicides with an activated halogen atom, such as chloroacetamide, bronopol and bronidox;

Tectamers, such as 2-bromo-2-nitro-1,3-propanediol, 2-bromo-4'-hydroxyacetophenone, 2,2-dibromo-3-nitrilepropionamide, 1,2-dibromo-2,4-dicyanobutane and β-bromo-β-nitrostyrene;

tetrachloro-4-methylsulfonylpyridine, pyrimethanol, mepanipyrim, dipyrithione;

metal soaps such as tin, copper and zinc naphthenate, tin, copper and zinc octoate, tin, copper and zinc 2-ethylhexanoate, tin, copper and zinc oleate, tin, copper and zinc phosphate and tin, copper and zinc benzoate;

metal salts such as copper hydroxycarbonate, sodium dichromate, potassium dichromate, potassium chromate, copper sulfate, copper chloride, copper borate, zinc fluorosilicate, copper fluorosilicate;

oxides such as tributyltin oxide, $Cu_2O$, CuO, ZnO;

dialkyldithiocarbamates, such as sodium and zinc salts of dialkyldithiocarbamates, tetramethylthiuram disulfide and potassium N-methyldithiocarbamate;

nitrites such as 2,4,5,6-tetrachloroisophthalodinitrile, disodium cyanodithioimidocarbamate;

quinolines, such as 8-hydroxyquinoline and its copper salts;

mucochloric acid, 5-hydroxy-2-(5H)-furanone;

4,5-dichlorodithiazolinone, 4,5-benzodithiazolinone, 4,5-trimethylenedithiazolinone;

4,5-dichloro-(3H)-1,2-dithiol-3-one, 3,5-dimethyltetrahydro-1,3,5-thiadiazine-2-thione, N-(2-p-chlorobenzoylethyl)hexaminium chloride, potassium N-hydroxymethyl-N'-methyldithiocarbamate;
2-oxo-2-(4-hydroxyphenyl)acetohydroximinoyl chloride;
phenyl 2-chlorocyanovinyl sulfone, phenyl 1,2-dichloro-2-cyanovinyl sulfone;
silver-, zinc- or copper-containing zeolites, alone or enclosed in polymeric active constituents;
algicides such as copper sulfate, dichlorophen, endothal, fentin acetate and quinoclamin;
herbicides such as acetochlor, acifluorfen, aclonifen, acrolein, alachlor, alloxydim, ametryn, amidosulfuron, amitrol, ammonium sulfate, anilofos, asulam, atrazine, aziprotryn, benazolin, benfluralin, benfuresate, bensulfuron, bensulide, benztazone, chloridazon, chlorimuron, chloromethoxyfen, chloronitrofen, chloroacetic acid, chloropicrin, chlorotoluron, chloroxuron, chloropropham, chlorosulfuron, chlorothal, chlorothiamide, cinmethyline, cinosulfuron, clethodim, clomazone, clomeprop, clopyralid, cyanamide, cyanazine, cycloate, cycloxydim, benzofencap, benzthiazuron, bifenox, bilanafos, borax, bromacil, bromobutide, bromofenoxim, bromoxynil, butachlor, butamifos, butanachlor, butralin, butylate, carbetamide, CGA 184927, chloramben, chlorobromuron, chlorobufam, chloroflurenol, difenoxuron, difenzoquat, diflufenican, dimefuron, dimepiperate, dimethachlor, dimethametryn, dimethipin, dimethylarsenic acid, dinitramin, dinoseb acetate, dinoseb, dinoterb, diphenamide, dipropetryn, diquat, dithiopyr, diuron, DNOC, PPX-A788, 2,4-D, daimuron, dalapon, dazomet, 2,4-DB, desmedipham, desmetryn, dicamba, dichlobenil, dichloroprop, dichloroprop-P, diclofop, diethatyl, flamprop-M, flazasulfuron, fluazifop, fluazifop-P, fluchloralin, flumeturon, fluoroglycofen, fluoronitrofen, flupropanate, flurenol, fluridon, fluorochloridon, fluroxypyr, fomosafen, fusamin, furyloxyfen, glufosinate, glyphosate, haloxyfop, hexazinon, imazamethabenz, imazapyr, imazaquin, imazethapyr, ioxynil, isopropalin, isoproturon, isouron, isoxaben, isoxapyrifop, lactofen, lenacil, linuron, LS830556, MCPA, pebulat, pendimethalin, pentachlorophenol, pentanochlor, mineral oil fractions, phenmedipham, picloram, piperophos, pretilachlor, primisulfuron, prodiamin, proglinazin, prometon, prometryn, propachlor, propanil, propaquizafop, propazir, propham, propyzamide, prosulfocarb, pyrazolynate, pyrazosulfuron, pyrazoxyfen, pyributicarb, pyridat, quinclorac, quinmerac, quinoclamin, quizalofop, quizalofop-P, S-23121, DPX-E96361, DSMA, eglinazine, endothal, epsorcarb, EPTC, ethalfluralin, ethidimuron, ethofumesate, fenoxaprop, fenoxaprop-P, fenuron, flamprop, irgarol 1051, MCPA-thioethyl, MCPB, mecoprop, mecoprop-P, mefenacet, mefluidid, metam, metamitron, metazachlor, methabenzthiazuron, methazole, methoprotryn, methyldymron, methyl isothiocyanate, metobromuron, metolachlor, metoxuron, metribuzin, metsulfuron, molinate, monoalid, monolinuron, MSMA, naproanilide, napropamide, naptalam, neburon, nicosulfuron, nipyraclofen, norflurazon, orbencarb, oryzalin, oxadiazon, oxyfluorfeno, paraquat, prometryn, simetryn, SMY 1500, sodium chlorate, sulfometuron, tar oils, TCA, tebutam, tebuthiuron, terbacil, terbumeton, terbuthylazine, terbutryn, thiazafluron, thifensulfuron, thiobencarb, thiocarbazil, tioclorim, tralkoxydim, tri-allate, triasulfuron, tribenzuron, triclopyr, tridiphane, trietazine, trifluralin, UB1-C4874, vernolate.

The biocide composition according to the invention may comprise further customary constituents, which are known as additives to the skilled worker in the biocides field. Examples of these are thickeners, antifoams, pH regulators, perfumes, dispersants and stabilizers such as buffers, zinc salts, zinc oxide and complexing agents.

When used in practice, the biocide composition can be introduced either as a ready mix or by separately adding the biocides and the remaining components of the composition to the system which is susceptible to microbial attack and to be preserved. In general, the total concentration of the biocides in the system which is susceptible to microbial attack and to be preserved is 0.01 to 10% in the case of, for example, colors, renders, plastics and leather. If the biocides are used as antifouling active ingredients, their total concentration in the system to be preserved is from 0.1 to 50%. In the event that the biocides are employed in timber preservation, they are normally used at a total concentration of from 0.1 to 20%. These concentrations refer in each case to the complete mixture of system to be preserved and biocide composition.

The examples illustrate the invention.

EXAMPLE 1

This example demonstrates the synergism of the combinations of zinc pyrithione (ZnPy), 3-iodo-2-propynyl N-butylcarbamate (IPBC) and 2-n-octylisothiazolin-3-one (OIT) in the biocide composition according to the invention.

To this end, aqueous mixtures with different concentrations of, on the one hand, a mixture of ZnPy and OIT (weight ratio 80:20) and, on the other hand, 3-iodo-2-propynyl N-butylcarbamate (IPBC) were prepared, and the effect of these mixtures on *Penicillium funiculosum* DSM 12637 was tested.

In addition to the biocide component and water, the aqueous mixtures also comprised a nutrient medium, viz. a Sabouraud maltose broth (commercial product, Merck No. 10393). The cell density was $10^6$ cells/ml. The incubation time was 96 hours at 25° C. Each sample was incubated in a shaker-incubator at 120 rpm.

Table I hereinbelow shows the concentrations of, on the one hand, the mixture of ZnPy and OIT and, on the other hand, of IPBC. It can also be seen from this table whether microbial growth took place (symbol "+") or not (symbol "−").

Thus, table I also shows the minimum inhibitory concentrations (MICs). Accordingly, an MIC value of 0.75 ppm results when only the mixture of ZnPy and OIT (weight ratio 80:20) is used, and an MIC value of 2 ppm when only IPBC is used. In contrast, the MIC values of mixtures of, on the one hand, ZnPy+OIT and, on the other hand, IPBC are markedly lower, that is to say the combination of these mixtures acts synergistically.

TABLE I

*Penicillium funiculosum* DSM 12637:
MIC values of ZnPy/OIT (80:20) + IPBC
at an incubation time of 96 h/25° C.

| ZnPy/OIT (80:20) concentration (ppm) | IPBC concentration (ppm) | | | | | | | | | | |
|---|---|---|---|---|---|---|---|---|---|---|---|
| | 3 | 2 | 1 | 0.75 | 0.5 | 0.4 | 0.3 | 0.2 | 0.1 | 0.05 | 0 |
| 5 | − | − | − | − | − | − | − | − | − | − | − |
| 3.0 | − | − | − | − | − | − | − | − | − | − | − |
| 2 | − | − | − | − | − | − | − | − | − | − | − |

TABLE I-continued

*Penicillium funiculosum* DSM 12637:
MIC values of ZnPy/OIT (80:20) + IPBC
at an incubation time of 96 h/25° C.

| ZnPy/OIT (80:20) concentration (ppm) | IPBC concentration (ppm) | | | | | | | | | |
|---|---|---|---|---|---|---|---|---|---|---|
| | 3 | 2 | 1 | 0.75 | 0.5 | 0.4 | 0.3 | 0.2 | 0.1 | 0.05 | 0 |
| 1 | – | – | – | – | – | – | – | – | – | – | – |
| 0.75 | – | – | – | – | – | – | – | – | – | – | – |
| 0.5 | – | – | – | – | – | – | – | – | – | – | – |
| 0.4 | – | – | – | – | – | – | – | – | – | + | + |
| 0.3 | – | – | – | – | + | + | + | + | + | + | + |
| 0.2 | – | – | – | – | + | + | + | + | + | + | + |
| 0.1 | – | – | – | – | + | + | + | + | + | + | + |
| 0.05 | – | – | – | + | + | + | + | + | + | + | + |
| 0 | – | – | + | + | + | + | + | + | + | + | + |

The synergism which is present is shown in the form of figures using the calculations of the synergistic index shown in table II. The synergistic index calculated by the method of F. C. Kull et al., Applied Microbiology, vol. 9 (1961), p. 538. Here, the synergistic index is calculated using the following formula:

$$\text{Synergistic index } SI = Q_a/Q_A + Q_b/Q_B.$$

When applying this formula to the biocide system tested in the present context, the parameters in the formula have the following meanings:

$Q_a$ = ZnPy concentration in the ZnPy/IPBC biocide mixture
$Q_A$ = concentration of ZnPy as the only biocide
$Q_b$ = IPBC concentration in the ZnPy/IPBC biocide mixture
$Q_B$ = concentration of IPBC as the only biocide.

If the synergistic index has a value of above 1, this means that antagonism is present. If the synergistic index assumes a value of 1, this means that an additive effect of the two biocides exists. If the synergistic index assumes a value of less than 1, this means that synergism of the two biocides exists.

Synergism was present when ZnPy/OIT (weight ratio 80:20), on the one hand, and IPBC, on the other hand, were employed simultaneously. The calculation of the synergistic index can be seen from table II. Accordingly, the lowest synergistic index for *Penicillium funiculosum* DSM 12637 (0.58) was found for a mixture of 11.8% by weight of ZnPy/OIT (80:20) and 88.2% by weight of IPBC.

TABLE II

*Penicillium funiculosum* DSM 12637:
calculation of the synergistic index of ZnPy/OIT (80:20) + IPBC
at an incubation time of 96 h/25° C.

| MIC at | | Total concentration of | Concentration | | | | |
|---|---|---|---|---|---|---|---|
| ZnPy/OIT (80:20) concentration $Q_a$ (ppm) | IPBC concentration $Q_b$ (ppm) | ZnPy/OIT + IPBC $Q_a + Q_b$ (ppm) | ZnPy/OIT (80:20) (% by weight) | IPBC (% by weight) | $Q_a/Q_A$ | $Q_b/Q_B$ | Synergistic index $Q_a/Q_A + Q_b/Q_B$ |
| 0 | 2 | 2 | 0.0 | 100.0 | 0.00 | 1.00 | 1.00 |
| 0.05 | 1 | 1.05 | 4.8 | 95.2 | 0.10 | 0.50 | 0.60 |
| 0.1 | 0.75 | 0.85 | 11.8 | 88.2 | 0.20 | 0.38 | 0.58 |
| 0.2 | 0.75 | 0.95 | 21.1 | 78.9 | 0.40 | 0.38 | 0.78 |
| 0.4 | 0.1 | 0.5 | 80.0 | 20.0 | 0.80 | 0.05 | 0.85 |
| 0.5 | 0 | 0.5 | 100.0 | 0.0 | 1.00 | 0.00 | 1.00 |

EXAMPLE 2

Analogously to example 1, the synergism of a mixture of ZnPy, IPBC and 4,5-dichloro-2-n-octyl-4-isothiazolin-3-one (DCOIT) was shown with regard to the microorganism *Penicillium funiculosum* DSM 12637. In each case, the weight ratio of ZnPy and DCOIT was 80:20.

Again, the experimental batches contained a Sabouraud maltose broth as the nutrient medium. The cell density was $10^6$ cells/ml. The incubation time was 96 hours at 25° C. Each sample was incubated in a shaker-incubator at 120 rpm.

The MIC values of biocide compositions tested can be seen from table III which follows. The MIC value was 0.50 ppm when only a ZnPy/DCOIT mixture (weight ratio 80:20) was employed and 2 ppm when only IPBC was employed.

TABLE III

*Penicillium funiculosum* DSM 12637:
MIC values of ZnPy/DCOIT (80:20) + IPBC
at an incubation time of 96 h/25° C.

| ZnPy/DCOIT (80:20) concentration (ppm) | IPBC concentration (ppm) | | | | | | | | | |
|---|---|---|---|---|---|---|---|---|---|---|
| | 3 | 2 | 1 | 0.75 | 0.5 | 0.4 | 0.3 | 0.2 | 0.1 | 0.05 | 0 |
| 5 | – | – | – | – | – | – | – | – | – | – | – |
| 3.0 | – | – | – | – | – | – | – | – | – | – | – |
| 2 | – | – | – | – | – | – | – | – | – | – | – |
| 1 | – | – | – | – | – | – | – | – | – | – | – |
| 0.75 | – | – | – | – | – | – | – | – | – | – | – |
| 0.5 | – | – | – | – | – | – | – | – | – | – | + |
| 0.4 | – | – | – | – | – | – | – | – | – | – | + |
| 0.3 | – | – | – | – | – | – | – | – | – | – | + |
| 0.2 | – | – | – | – | – | – | – | – | + | + | + |
| 0.1 | – | – | – | + | + | + | + | + | + | + | + |
| 0.05 | – | – | – | + | + | + | + | + | + | + | + |
| 0 | – | – | + | + | + | + | + | + | + | + | + |

Synergism was present when ZnPy/DCOIT (weight ratio 80:20), on the one hand, and IPBC, on the other hand, were employed simultaneously. The calculation of the synergistic index can be seen from table IV. Accordingly, the lowest synergistic index for *Penicillium funiculosum* DSM 12637 (0.50) was found for a mixture of 50.0% by weight of ZnPy/DCOIT (80:20) and 50.0% by weight of IPBC.

TABLE IV

*Penicillium funiculosum* DSM 12637: calculation of the synergistic index of ZnPy/DCOIT (80:20) + IPBC at an incubation time of 96 h/25° C.

| ZnPy/DCOIT (80:20) concentration $Q_a$ (ppm) | IPBC concentration $Q_b$ (ppm) | Total concentration of ZnPy/DCOIT + IPBC $Q_a + Q_b$ (ppm) | ZnPy/DCOIT (80:20) (% by weight) | IPBC (% by weight) | $Q_a/Q_A$ | $Q_b/Q_B$ | Synergistic index $Q_a/Q_A + Q_b/Q_B$ |
|---|---|---|---|---|---|---|---|
| 0 | 2 | 2 | 0.0 | 100.0 | 0.00 | 1.00 | 1.00 |
| 0.05 | 1 | 1.05 | 4.8 | 95.2 | 0.10 | 0.50 | 0.60 |
| 0.1 | 0.75 | 0.85 | 11.8 | 88.2 | 0.20 | 0.20 | 0.58 |
| 0.2 | 0.4 | 0.6 | 33.3 | 66.7 | 0.40 | 0.15 | 0.60 |
| 0.2 | 0.3 | 0.5 | 40.0 | 60.0 | 0.40 | 0.10 | 0.55 |
| 0.2 | 0.2 | 0.4 | 50.0 | 50.0 | 0.40 | 0.05 | 0.50 |
| 0.3 | 0.1 | 0.4 | 75.0 | 25.0 | 0.60 | 0.03 | 0.65 |
| 0.3 | 0.05 | 0.35 | 85.7 | 14.3 | 0.60 | 0.03 | 0.63 |
| 0.4 | 0.05 | 0.45 | 88.9 | 11.1 | 0.80 | 0.00 | 0.83 |
| 0.5 | 0 | 0.5 | 100.0 | 0.0 | 1.00 | 0.00 | 1.00 |

EXAMPLE 3

Analogously to example 1, the synergism of ZnPy and OIP was shown with regard to the microorganism *Penicillium funiculasum* DSM 12637.

Again, the experimental batches contained a Sabouraud maltose broth as the nutrient medium. The cell density was $10^6$ cells/ml. The incubation time was 96 hours at 25° C. Each sample was incubated in a shaker-incubator at 120 rpm.

The MIC values of the biocide composition tested can be seen from table V which follows. The MIC value was 2 ppm when only ZnPy was employed and 0.5 ppm when only OIT was employed.

TABLE V

*Penicillium funiculosum* DSM 12637: MIC values of ZnPy + OIT at an incubation time of 96 h/25° C.

| ZnPy concentration (ppm) | OIT concentration (ppm) | | | | | | | | | |
|---|---|---|---|---|---|---|---|---|---|---|
| | 3 | 2 | 1 | 0.75 | 0.5 | 0.4 | 0.3 | 0.2 | 0.1 | 0 |
| 5 | − | − | − | − | − | − | − | − | − | − |
| 3.0 | − | − | − | − | − | − | − | − | − | − |
| 2 | − | − | − | − | − | − | − | − | − | − |
| 1 | − | − | − | − | − | − | − | − | − | + |
| 0.75 | − | − | − | − | − | − | − | − | − | + |
| 0.5 | − | − | − | − | − | − | − | − | + | + |
| 0.4 | − | − | − | − | − | − | − | − | + | + |
| 0.3 | − | − | − | − | − | − | − | + | + | + |
| 0.2 | − | − | − | − | − | − | + | + | + | + |
| 0.1 | − | − | − | − | − | + | + | + | + | + |
| 0 | − | − | − | − | − | + | + | + | + | + |

Synergism was present when ZnPy and OIT were employed simultaneously. The calculation of the synergistic index can be seen from table VI. Accordingly, the lowest synergistic index (0.58) for *Penicillium funiculosum* DSM 12637 was found for a mixture of 88.2% by weight of ZnPy and 11.8% by weight of OIT.

TABLE VI

*Penicillium funiculosum* DSM 12637: calculation of the synergistic index of ZnPy + OIT at an incubation time of 96 h/25° C.

| ZnPy concentration $Q_a$ (ppm) | OIT concentration $Q_b$ (ppm) | Total concentration ZnPy + OIT $Q_a + Q_b$ (ppm) | ZnPy (% by weight) | OIT (% by weight) | $Q_a/Q_A$ | $Q_b/Q_B$ | Synergistic index $Q_a/Q_A + Q_b/Q_B$ |
|---|---|---|---|---|---|---|---|
| 0 | 0.5 | 0.5 | 0.0 | 100.0 | 0.00 | 1.00 | 1.00 |
| 0.2 | 0.4 | 0.6 | 33.3 | 66.7 | 0.10 | 0.80 | 0.90 |
| 0.3 | 0.3 | 0.6 | 50.0 | 50.0 | 0.15 | 0.60 | 0.75 |
| 0.4 | 0.2 | 0.6 | 66.7 | 33.3 | 0.20 | 0.40 | 0.60 |
| 0.5 | 0.2 | 0.7 | 71.4 | 28.6 | 0.25 | 0.40 | 0.65 |
| 0.75 | 0.1 | 0.85 | 88.2 | 11.8 | 0.38 | 0.20 | 0.58 |
| 1 | 0.1 | 1.1 | 90.9 | 9.1 | 0.50 | 0.20 | 0.70 |
| 2 | 0 | 2 | 100.0 | 0.0 | 1.00 | 0.00 | 1.00 |

EXAMPLE 4

Analogously to example 1, the synergism of ZnPy and OIT was shown with regard to the microorganism *Penicillium funiculosum* IMI 211742.

Again, the experimental batches contained a Sabouraud maltose broth as the nutrient medium. The cell density was $10^6$ cells/ml. The incubation time was 72 hours at 25° C. Each sample was incubated in a shaker-incubator at 120 rpm.

The MIC values of the biocide composition tested can be seen from table VII which follows. The MIC value was 1 ppm when only ZnPy was employed and 0.75 ppm when only IPBC was employed.

TABLE VII

*Penicillium funiculosum* IMI 211742: MIC values of ZnPy + OIT at an incubation time of 72 h/25° C.

| ZnPy concentration (ppm) | OIT concentration (ppm) | | | | | | | | | |
|---|---|---|---|---|---|---|---|---|---|---|
| | 3 | 2 | 1 | 0.75 | 0.5 | 0.4 | 0.3 | 0.2 | 0.1 | 0 |
| 5 | − | − | − | − | − | − | − | − | − | − |
| 3.0 | − | − | − | − | − | − | − | − | − | − |
| 2 | − | − | − | − | − | − | − | − | − | − |
| 1 | − | − | − | − | − | − | − | − | − | − |
| 0.75 | − | − | − | − | − | − | − | − | − | + |
| 0.5 | − | − | − | − | − | − | − | − | − | + |
| 0.4 | − | − | − | − | − | − | − | + | + | + |
| 0.3 | − | − | − | − | − | − | + | + | + | + |
| 0.2 | − | − | − | − | + | + | + | + | + | + |
| 0.1 | − | − | − | − | + | + | + | + | + | + |
| 0 | − | − | − | − | + | + | + | + | + | + |

Synergism was present when ZnPy and OIT were employed simultaneously. The calculation of the synergistic index can be seen from table VIII. Accordingly, the lowest synergistic index (0.63) for *Penicillium funiculosum* IMI 211742 was found for a mixture of 83.3% by weight of ZnPy and 16.7% by weight of OIT.

TABLE VIII

*Penicillium funiculosum* IMI 211742: calculation of the synergistic index of ZnPy + OIT at an incubation time of 72 h/25° C.

| ZnPy concentration $Q_a$ (ppm) | OIT concentration $Q_b$ (ppm) | MIC at Total concentration ZnPy + OIT $Q_a + Q_b$ (ppm) | Concentration ZnPy (% by weight) | Concentration OIT (% by weight) | $Q_a/Q_A$ | $Q_b/Q_B$ | Synergistic index $Q_a/Q_A + Q_b/Q_B$ |
|---|---|---|---|---|---|---|---|
| 0 | 0.75 | 0.75 | 0.0 | 100.0 | 0.00 | 1.00 | 1.00 |
| 0.3 | 0.5 | 0.8 | 37.5 | 62.5 | 0.30 | 0.67 | 0.97 |
| 0.3 | 0.4 | 0.7 | 42.9 | 57.1 | 0.30 | 0.53 | 0.83 |
| 0.4 | 0.3 | 0.7 | 57.1 | 42.9 | 0.40 | 0.40 | 0.80 |
| 0.5 | 0.2 | 0.7 | 71.4 | 28.6 | 0.50 | 0.27 | 0.77 |
| 0.5 | 0.1 | 0.6 | 83.3 | 16.7 | 0.50 | 0.13 | 0.63 |
| 0.75 | 0.1 | 0.85 | 88.2 | 11.8 | 0.75 | 0.13 | 0.88 |
| 1 | 0 | 1 | 100.3 | 0.0 | 1.00 | 0.00 | 1.00 |

EXAMPLE 5

Analogously to example 1, the synergism of ZnPy and DCOIT was shown with regard to the microorganism *Penicillium funiculosum* DSM 12637.

Again, the experimental batches contained a Sabouraud maltose broth as the nutrient medium. The cell density was $10^6$ cells/ml. The incubation time was 96 hours at 25° C. Each sample was incubated in a shaker-incubator at 120 rpm.

The MIC values of the biocide composition tested can be seen from table IX which follows. The MIC value was 2 ppm when only ZnPy was employed and 2 ppm when only DCOIT was employed.

TABLE IX

*Penicillium funiculosum* DSM 12637: MIC values of ZnPy + DCOIT at an incubation time of 96 h/25° C.

| ZnPy concentration (ppm) | DCOIT concentration (ppm) | | | | | | | | |
|---|---|---|---|---|---|---|---|---|---|
| | 3 | 2 | 1 | 0.75 | 0.5 | 0.4 | 0.3 | 0.2 | 0.1 | 0 |
| 5 | – | – | – | – | – | – | – | – | – | – |
| 3.0 | – | – | – | – | – | – | – | – | – | – |
| 2 | – | – | – | – | – | – | – | – | – | – |
| 1 | – | – | – | – | – | – | – | – | – | + |
| 0.75 | – | – | – | – | – | – | – | – | – | + |
| 0.5 | – | – | – | – | – | – | – | – | + | + |
| 0.4 | – | – | – | – | – | – | – | + | + | + |
| 0.3 | – | – | – | – | – | + | + | + | + | + |
| 0.2 | – | – | – | + | + | + | + | + | + | + |
| 0.1 | – | – | + | + | + | + | + | + | + | + |
| 0 | – | – | + | + | + | + | + | + | + | + |

Synergism was present when ZnPy and DCOIT were employed simultaneously. The calculation of the synergistic index can be seen from table X. Accordingly, the lowest synergistic index (0.35) for *Penicillium funiculosum* DSM 12637 was found for a mixture of 57.1% to 71% by weight of ZnPy and 42.9% to 28.6% by weight of DCOIT.

TABLE X

*Penicillium funiculosum* DSM 12637: calculation of the synergistic index of ZnPy +DCOIT at an incubation time of 96 h/25° C.

| ZnPy concentration $Q_a$ (ppm) | DCOIT concentration $Q_b$ (ppm) | MIC at Total concentration ZnPy + DCOIT $Q_a + Q_b$ (ppm) | Concentration ZnPy (% by weight) | Concentration DCOIT (% by weight) | $Q_a/Q_A$ | $Q_b/Q_B$ | Synergistic index $Q_a/Q_A + Q_b/Q_B$ |
|---|---|---|---|---|---|---|---|
| 0 | 2 | 2 | 0.0 | 100.0 | 0.00 | 1.00 | 1.00 |
| 0.2 | 1 | 1.2 | 16.7 | 83.3 | 0.10 | 0.50 | 0.60 |
| 0.3 | 0.75 | 1.05 | 28.6 | 71.4 | 0.15 | 0.38 | 0.53 |
| 0.3 | 0.5 | 0.8 | 37.5 | 62.5 | 0.15 | 0.25 | 0.40 |
| 0.4 | 0.4 | 0.8 | 50.0 | 50.0 | 0.20 | 0.20 | 0.40 |
| 0.4 | 0.3 | 0.7 | 57.1 | 42.9 | 0.20 | 0.15 | 0.35 |
| 0.5 | 0.2 | 0.7 | 71.4 | 28.6 | 0.25 | 0.10 | 0.35 |
| 0.75 | 0.1 | 0.85 | 88.2 | 11.8 | 0.38 | 0.05 | 0.43 |
| 1 | 0.1 | 1.1 | 90.9 | 9.1 | 0.50 | 0.05 | 0.55 |
| 2 | 0 | 2 | 100.0 | 0.0 | 1.00 | 0.00 | 1.00 |

EXAMPLE 6

Analogously to example 1, the synergism of ZnPy and DCOIT was shown with regard to the microorganism *Penicillium funiculosum* IMI 211742.

Again, the experimental batches contained a Sabouraud maltose broth as the nutrient medium. The cell density was $10^6$ cells/ml. The incubation time was 72 hours at 25° C. Each sample was incubated in a shaker-incubator at 120 rpm.

The MIC values of the biocide composition tested can be seen from table XI which follows. The MIC value was 0.75 ppm when only ZnPy was employed and 1 ppm when only DCOIT was employed.

TABLE XI

*Penicillium funiculosum* IMI 211742: MIC values of ZnPy + DCOIT at an incubation time of 72 h/25° C.

| ZnPy concentration (ppm) | DCOIT concentration (ppm) | | | | | | | | |
|---|---|---|---|---|---|---|---|---|---|
| | 3 | 2 | 1 | 0.75 | 0.5 | 0.4 | 0.3 | 0.2 | 0.1 | 0 |
| 5 | – | – | – | – | – | – | – | – | – | – |
| 3.0 | – | – | – | – | – | – | – | – | – | – |
| 2 | – | – | – | – | – | – | – | – | – | – |
| 1 | – | – | – | – | – | – | – | – | – | – |
| 0.75 | – | – | – | – | – | – | – | – | – | – |
| 0.5 | – | – | – | – | – | – | – | – | + | + |
| 0.4 | – | – | – | – | – | – | – | – | + | + |
| 0.3 | – | – | – | – | – | – | + | + | + | + |
| 0.2 | – | – | – | – | – | + | + | + | + | + |
| 0.1 | – | – | – | – | + | + | + | + | + | + |
| 0 | – | – | – | + | + | + | + | + | + | + |

Synergism was present when ZnPy and DCOIT were employed simultaneously. The calculation of the synergistic index can be seen from table XII. Accordingly, the lowest synergistic index (0.73) for *Penicillium funiculosum* IMI 211742 was found for a mixture of 66.7% by weight of ZnPy and 33.3% by weight of DCOIT.

TABLE XII

*Penicillium funiculosum* IMI 211742: calculation of the synergistic index of ZnPy + DCOIT at an incubation time of 72 h/25° C.

| ZnPy concentration $Q_a$ (ppm) | DCOIT concentration $Q_b$ (ppm) | MIC at Total concentration ZnPy + DCOIT $Q_a + Q_b$ (ppm) | Concentration ZnPy (% by weight) | Concentration DCOIT (% by weight) | $Q_a/Q_A$ | $Q_b/Q_B$ | Synergistic index $Q_a/Q_A + Q_b/Q_B$ |
|---|---|---|---|---|---|---|---|
| 0 | 1 | 1 | 0.0 | 100.0 | 0.00 | 1.00 | 1.00 |
| 0.1 | 0.75 | 0.85 | 11.8 | 88.2 | 0.13 | 0.75 | 0.88 |
| 0.2 | 0.5 | 0.7 | 28.6 | 71.4 | 0.27 | 0.50 | 0.77 |
| 0.3 | 0.4 | 0.7 | 42.9 | 57.1 | 0.40 | 0.40 | 0.80 |
| 0.4 | 0.3 | 0.7 | 57.1 | 42.9 | 0.53 | 0.30 | 0.83 |
| 0.4 | 0.2 | 0.6 | 66.7 | 33.3 | 0.53 | 0.20 | 0.73 |
| 0.5 | 0.2 | 0.7 | 71.4 | 28.6 | 0.67 | 0.20 | 0.87 |
| 0.75 | 0 | 0.75 | 100.0 | 0.0 | 1.00 | 0.00 | 1.00 |

EXAMPLE 7

Analogously to example 1, the synergism of ZnPy and DCOIT was shown with regard to the microorganism *Aspergillus niger* DSM 1957.

Again, the experimental batches contained a Sabouraud maltose broth as the nutrient medium. The cell density was $10^6$ cells/ml. The incubation time was 72 hours at 25° C. Each sample was incubated in a shaker-incubator at 120 rpm.

The MIC values of the biocide compositions tested can be seen from table XIII which follows. The MIC value was 17.5 ppm when only ZnPy was employed and 0.75 ppm when only DCOIT was employed.

TABLE XIII

*Aspergillus niger* DSM 1957: MIC values of ZnPy + DCOIT at an incubation time of 72 h/25° C.

| ZnPy concentration (ppm) | IPBC concentration (ppm) | | | | | | | | | | |
|---|---|---|---|---|---|---|---|---|---|---|---|
| | 5 | 4 | 3 | 2 | 1 | 0.75 | 0.5 | 0.4 | 0.3 | 0.2 | 0.1 | 0 |
| 20 | − | − | − | − | − | − | − | − | − | − | − | − |
| 17.5 | − | − | − | − | − | − | − | − | − | − | − | − |
| 15.0 | − | − | − | − | − | − | − | − | − | + | + | + |
| 12.5 | − | − | − | − | − | − | − | − | − | + | + | + |
| 10 | − | − | − | − | − | − | − | − | − | + | + | + |
| 7.5 | − | − | − | − | − | − | − | − | − | + | + | + |
| 5 | − | − | − | − | − | − | − | − | − | + | + | + |
| 4 | − | − | − | − | − | − | − | + | + | + | + | + |
| 3 | − | − | − | − | − | − | − | + | + | + | + | + |
| 2 | − | − | − | − | − | − | − | + | + | + | + | + |
| 1 | − | − | − | − | − | − | + | + | + | + | + | + |
| 0 | − | − | − | − | − | − | + | + | + | + | + | + |

Synergism was present when ZnPy and DCOIT were employed simultaneously. The calculation of the synergistic index can be seen from table XIV. Accordingly, the lowest synergistic index (0.69) for *Aspergillus niger* DSM 1957 was found for a mixture of 94.3% by weight of ZnPy and 5.7% by weight of DCOIT.

TABLE XIV

*Aspergillus niger* DSM 1957: calculation of the synergistic index of ZnPy + DCOIT at an incubation time of 72 h/25° C.

| ZnPy concentration $Q_a$ (ppm) | DCOIT concentration $Q_b$ (ppm) | MIC at Total concentration ZnPy + DCOIT $Q_a + Q_b$ (ppm) | Concentration ZnPy (% by weight) | Concentration DCOIT (% by weight) | $Q_a/Q_A$ | $Q_b/Q_B$ | Synergistic index $Q_a/Q_A + Q_b/Q_B$ |
|---|---|---|---|---|---|---|---|
| 0 | 0.75 | 0.75 | 0.0 | 100.0 | 0.00 | 1.00 | 1.00 |
| 1 | 0.5 | 1.5 | 66.7 | 33.3 | 0.06 | 0.67 | 0.72 |
| 2 | 0.5 | 2.5 | 80.0 | 20.0 | 0.11 | 0.67 | 0.78 |
| 3 | 0.5 | 3.5 | 85.7 | 14.3 | 0.17 | 0.67 | 0.84 |
| 4 | 0.5 | 4.5 | 88.9 | 11.1 | 0.23 | 0.67 | 0.90 |
| 5 | 0.4 | 5.4 | 92.6 | 7.4 | 0.29 | 0.53 | 0.82 |
| 5 | 0.3 | 5.3 | 94.3 | 5.7 | 0.29 | 0.40 | 0.69 |
| 7.5 | 0.3 | 7.8 | 96.2 | 3.8 | 0.43 | 0.40 | 0.83 |
| 10 | 0.3 | 10.3 | 97.1 | 2.9 | 0.57 | 0.40 | 0.97 |
| 17.5 | 0 | 17.5 | 100.0 | 0.0 | 1.00 | 0.00 | 1.00 |

EXAMPLES 8 TO 13

To test the fungicidal and algicidal film preservation of coating materials, samples of these materials had different concentrations of biocides added to them and were applied to suitable support materials, for example to calcium silicate sheets in a size of approximately 5 cm×5 cm, using a brush or a spatula. After the coatings had dried at 20±1° C., they were exposed to water during a specific period.

When the fungicidal preservation was tested, the test objects which had been exposed to water or not were embedded in an agar nutrient medium, the sample surface not being covered by the nutrient medium. The embedded test objects were subsequently sprayed with a suspension of spores of fungi which are relevant under practice conditions and stored under optimal growth conditions for fungi.

To test the algicidal preservation, the test objects which had been exposed to water or not were placed into a specific nutrient solution for algae which contained selected algal species which are relevant for practice conditions and then stored under growth conditions which are optimal for algae. After the respected storage, the extent of fungal or algal growth on the surfaces of the test object was assessed.

In the tests for fungicidal preservation, a representative spore mixture of equal parts of the following species was used:

*Alternaria alternata*

*Aspergillus niger*

*Cladosporium cladosporoides*

*Penicillium funiculosum*

*Ulocladium atrum*

Key o=no visible growth x=minimal growth (covers up to 25% of the area)

xx=slight growth (covers up to 50% of the area)

xxx=moderate growth (covers up to 75% of the area)

xxxx=copious growth (covers up to 100% of the area)

In examples 8 to 10, the fungicidal and algicidal preservation of a matt exterior paint which is composed as shown in table XV hereinbelow was tested.

TABLE XV

Exterior paint

| Component | Amount in parts by weight |
|---|---|
| Water | 65 |
| Pigmentverteiler A (BASF AG) | 3 |
| Sodium polyphosphate, 25% strength solution | 4 |
| Concentrated ammonia | 2 |
| Preservative ACTICIDE ® FI (Thor GmbH) | 3 |
| 2% strength methylcellulose solution, 20000 mPas | 100 |
| White spirit (180–210° C.) | 13 |
| Lusolvan ® FBH (BASF AG) | 7 |
| Lumiten ® N-OC 30 (BASF AG) | 10 |
| Titanium dioxide rutile, Kronos ® 2043 (Kronos-Titan GmbH) | 180 |
| Omyacarb ® 5 GU (Omya GmbH) | 240 |
| Talc, 5 μm | 50 |
| Antifoam Agitan ® 280 (Münzing Chemie GmbH) | 3 |
| Polyacrylate Acronal ® 290D (BASF AG) | 320 |
| | 1000 |

In examples 11 to 13, the fungicidal and algicidal preservation of a float-finish rendering which is composed as shown in table XVI hereinbelow was tested:

TABLE XVI

Float-finish rendering

| Component | Amount in parts by weight |
|---|---|
| 25% strength sodium polyphosphate solution | 8 |
| Preservative ACTICIDE ® FI (Thor GmbH) | 3 |
| Antifoam Agitan ® 280 (Münzig Chemie GmbH) | 3 |
| Polyacrylate Latekoll ® D, 8% ammoniacal solution (BASF AG) | 8 |
| White spirit (180–210° C.) | 10 |
| Butyl diglycol | 10 |
| Basophob ® WDS (BASF AG) | 6 |
| Titanium dioxide rutile, Kronos ® 2044 (Kronos-Titan GmbH) | 28 |
| Omyacarb ® 40 GU (Omya GmbH) | 395 |
| Omyacarb ® 130 GU (Omya GmbH) | 255 |
| Plastorit (Luzenac Deutschland GmbH) | 65 |
| Quartz pebbles | 45 |
| Water | 32 |
| Acronal 290 D | 132 |
| | 1000 |

EXAMPLE 8

A film of the above exterior paint was tested for its preservation properties.

The biocide composition employed was the aqueous biocide composition I which follows. The percentages started refer to the entire aqueous mixture of exterior paint and active ingredients.

Biocide Composition I:

| ZnPy | 3% |
|---|---|
| IPBC | 2% |
| OIT | 3% |

Table XVII which follows states the amounts of active ingredients used in the experiments, the period for which the biocide-preserved films were exposed to water and the fungal and algal growth on the surface of the films at the end of the experiment.

TABLE XVII

Preservation of films of the above-mentioned exterior paint against fungal and algal growth using biocide composition I

| No. | Amounts of active ingredient ZnPy/IPBC/OIT (ppm) | Exposure to water (d) | Fungal growth on the film surface | Algal growth on the film surface |
|---|---|---|---|---|
| 1 | 30/20/30 | 0 | x | xxx |
| 2 | 30/20/30 | 2 | xx | xxxx |
| 3 | 60/40/60 | 0 | x | xx |
| 4 | 60/40/60 | 2 | xxx | xxxx |
| 5 | 90/60/90 | 0 | x | 0 |
| 6 | 90/60/90 | 2 | x | xxx |
| 7 | 150/100/150 | 0 | 0 | 0 |
| 8 | 150/100/150 | 2 | 0 | xxx |
| 9 | 225/150/225 | 0 | 0 | 0 |
| 10 | 225/150/225 | 2 | 0 | xx |
| 11 | 300/200/300 | 0 | 0 | 0 |
| 12 | 300/200/300 | 2 | 0 | 0 |
| 13 | 0/0/0 (comparison) | 0 | xxx | xxxx |
| 14 | 0/0/0 (comparison) | 2 | xxx | xxxx |

EXAMPLE 9

Example 8 was repeated, except that the aqueous biocide composition II hereinbelow was used. The percentages stated refer to the entire aqueous mixture of exterior paint and active ingredients.

Biocide Composition II:

| ZnPy | 3% |
|---|---|
| IPBC | 2% |
| DCOIT | 3% |

Table XVIII which follows states the amounts of active ingredients used in the experiments, the period for which the biocide-preserved films were exposed to water and the fungal and algal growth on the surface of the films at the end of the experiment.

TABLE XVIII

Preservation of films of the above-mentioned exterior paint against fungal and algal growth. using biocide composition II

| No. | Amounts of active ingredient ZnPy/IPBC/DCOIT (ppm) | Exposure to water (d) | Fungal growth on the film surface | Algal growth on the film surface |
|---|---|---|---|---|
| 1 | 30/20/30 | 0 | x | xxxx |
| 2 | 30/20/30 | 2 | xxx | xxxx |
| 3 | 60/40/60 | 0 | x | xx |
| 4 | 60/40/60 | 2 | xx | xxxx |
| 5 | 90/60/90 | 0 | 0 | xx |
| 6 | 90/60/90 | 2 | 0 | xxxx |
| 7 | 150/100/150 | 0 | 0 | x |
| 8 | 150/100/150 | 2 | 0 | xxxx |
| 9 | 225/150/225 | 0 | 0 | 0 |
| 10 | 225/150/225 | 2 | 0 | xx |
| 11 | 300/200/300 | 0 | 0 | 0 |
| 12 | 300/200/300 | 2 | 0 | 0 |
| 13 | 0/0/0 (comparison) | 0 | xxx | xxxx |
| 14 | 0/0/0 (comparison) | 2 | xxx | xxxx |

EXAMPLE 10

Example 8 was repeated, except that the aqueous biocide composition III hereinbelow was used. The percentages stated refer to the entire aqueous mixture of exterior paint and active ingredients.

Biocide Composition III:

| | |
|---|---|
| ZnPy | 3% |
| IPBC | 2% |
| OIT | 1.5% |
| DCOIT | 1.5% |

Table XIX which follows states the amounts of active ingredients used in the experiments, the period for which the biocide-preserved films were exposed to water and the fungal and algal growth on the surface of the films at the end of the experiment.

TABLE XIX

Preservation of films of the above-mentioned exterior paint against fungal and algal growth using biocide composition III

| No. | Amounts of active ingredient ZnPy/IPBC/OIT/DCOIT (ppm) | Exposure to water (d) | Fungal growth on the film surface | Algal growth on the film surface |
|---|---|---|---|---|
| 1 | 30/20/15/15 | 0 | x | xx |
| 2 | 30/20/15/15 | 2 | xx | xxxx |
| 3 | 60/40/30/30 | 0 | x | xx |
| 4 | 60/40/30/30 | 2 | xx | xxxx |
| 5 | 90/60/45/45 | 0 | 0 | 0 |
| 6 | 90/60/45/45 | 2 | 0 | xx |
| 7 | 150/100/75/75 | 0 | 0 | 0 |
| 8 | 150/100/75/75 | 2 | 0 | x |
| 9 | 225/150/112.5/112.5 | 0 | 0 | 0 |
| 10 | 225/150/112.5/112.5 | 2 | 0 | 0 |
| 11 | 300/200/150/150 | 0 | 0 | 0 |
| 12 | 300/200/150/150 | 2 | 0 | 0 |
| 13 | 0/0/0 (comparison) | 0 | xxx | xxxx |
| 14 | 0/0/0 (comparison) | 2 | xxx | xxxx |

EXAMPLE 11

Example 8 was repeated, but the above-mentioned float-finish rendering was used instead of the exterior paint.

The results are compiled in table XX which follows.

TABLE XX

Preservation of films of the above-mentioned float-finish rendering against fungal and algal growth using biocide composition I

| No. | Amounts of active ingredient ZnPy/IPBC/OIT (ppm) | Exposure to water (d) | Fungal growth on the film surface | Algal growth on the film surface |
|---|---|---|---|---|
| 1 | 30/20/30 | 0 | 0 | 0 |
| 2 | 30/20/30 | 2 | 0 | xxxx |
| 3 | 60/40/60 | 0 | 0 | 0 |
| 4 | 60/40/60 | 2 | 0 | 0 |
| 5 | 90/60/90 | 0 | 0 | 0 |
| 6 | 90/60/90 | 2 | 0 | 0 |
| 7 | 150/100/150 | 0 | 0 | 0 |
| 8 | 150/100/150 | 2 | 0 | 0 |
| 9 | 225/150/225 | 0 | 0 | 0 |
| 10 | 225/150/225 | 2 | 0 | 0 |
| 11 | 0/0/0 (comparison) | 0 | xxx | xxxx |
| 12 | 0/0/0 (comparison) | 2 | xxx | xxxx |

EXAMPLE 12

Example 11 was repeated, except that the aqueous biocide composition II was used.

The results are compiled in table XXI which follows.

TABLE XXI

Preservation of films of the above-mentioned float-finish rendering against fungal and algal growth using biocide composition II

| No. | Amounts of active ingredient ZnPy/IPBC/DCOIT (ppm) | Exposure to water (d) | Fungal growth on the film surface | Algal growth on the film surface |
|---|---|---|---|---|
| 1 | 30/20/30 | 0 | x | 0 |
| 2 | 30/20/30 | 2 | x | xxx |
| 3 | 60/40/60 | 0 | x | 0 |
| 4 | 60/40/60 | 2 | x | x |
| 5 | 90/60/90 | 0 | 0 | 0 |
| 6 | 90/60/90 | 2 | 0 | 0 |
| 7 | 150/100/150 | 0 | 0 | 0 |
| 8 | 150/100/150 | 2 | 0 | 0 |
| 9 | 225/150/225 | 0 | 0 | 0 |
| 10 | 225/150/225 | 2 | 0 | 0 |
| 11 | 0/0/0 (comparison) | 0 | xxx | xxxx |
| 12 | 0/0/0 (comparison) | 2 | xxx | xxxx |

EXAMPLE 13

Example 11 was repeated, except that the aqueous biocide composition III was used.

The results are compiled in table XXII which follows.

TABLE XXII

Preservation of films of the above-mentioned float-finish rendering against fungal and algal growth using biocide composition III

| No. | Amounts of active ingredient ZnPy/IPBC/OIT/DCOIT (ppm) | Exposure to water (d) | Fungal growth on the film surface | Algal growth on the film surface |
|---|---|---|---|---|
| 1 | 30/20/15/15 | 0 | xxx | xxxx |
| 2 | 30/20/15/15 | 2 | xx | xxxx |
| 3 | 60/40/30/30 | 0 | 0 | 0 |
| 4 | 60/40/30/30 | 2 | 0 | 0 |
| 5 | 90/60/45/45 | 0 | 0 | 0 |
| 6 | 90/60/45/45 | 2 | 0 | 0 |
| 7 | 150/100/75/75 | 0 | 0 | 0 |
| 8 | 150/100/75/75 | 2 | 0 | 0 |
| 9 | 225/150/112.5/112.5 | 0 | 0 | 0 |
| 10 | 225/150/112.5/112.5 | 2 | 0 | 0 |
| 11 | 0/0/0 (comparison) | 0 | xxx | xxxx |
| 12 | 0/0/0 (comparison) | 2 | xxx | xxxx |

We claim:

1. A biocide composition as additive to materials capable of being attacked by harmful microorganisms, comprising as biocidal active ingredients zinc pyrithione and 3-iodo-2-propinyl-N-butylacarbamate as well as 2-n-octylisothiazolin-3-one or 4,5-dichloro-2-n-octylisothiazolin-3-one or a mixture of both.

2. A biocide composition as claimed in claim 1, characterized in that the pyrithione is present in a concentration of from 0.5 to 99.5% by weight based on the entire biocide composition.

3. A biocide composition as claimed in claims 1 or 2, characterized in that isothiazolin-3-one or isothiazolin-3-ones is/are present in a concentration of from 0.1 to 99.9% by weight based on the entire biocide composition.

4. A biocide composition as claimed in any of claims 1 to 2, characterized in that the pyrithione and the isothiazolin-3-one are present in a weight ratio of from 1:1 000 to 1 000:1.

5. A biocide composition as claimed in claim 4, characterized in that the pyrithione and the 2-n-octylisothiazolin-3-one and/or 4,5-dichloro-2-n-octylisothiazolin-3-one are present in a weight ratio of from 1:10 to 10:1.

6. A biocide composition as claimed in any of claims 1 to 2, characterized in that the pyrithione and the isothiazolin-3-one or the isothiazolin-3-ones are present in a total concentration of from 0.2 to 100% by weight, based on the entire biocide composition.

7. A method of controlling harmful microorganisms in environments which are susceptible to attack by microorganisms, said method comprising applying an effective amount of a biocide composition as claimed in any of claims 1 or 2 to control said harmful microorganisms in environments which are susceptible to attack by microorganisms.

8. A method of controlling harmful microorganisms in systems as defined in claim 7 wherein the biocide composition is employed for preserving coatings, leather, plastics or timber.

9. A composition or material, preserved against harmful microorganisms, which is characterized by a content of a biocide composition as claimed in any of claims 1 to 2.

10. A biocide composition as additive to materials capable of being attacked by harmful microorganisms, said composition consisting essentially of zinc pyrithione and 3-iodo-2-propinyl-N-butylcarbamate and either 2-n-octylisothiazolin-3-one or 4,5-dichloro-2-n-octylisothiazolin-3-one or a mixture of both 2-n-octylisothiazolin-3-one and 4,5-dichloro-2-n-octylisothiazolin-3-one.

11. A biocide composition as additive to materials capable of being attacked by harmful microorganisms, said biocide composition consisting essentially of as biocidal active ingredients zinc pyrithione and 3-iodo-2-propinyl-N-butylcarbamate as well as 2-n-octylisothiazolin-3-one or 4,5-dichloro-2-n-octylisothiazolin-3-one or a mixture of both.

* * * * *